(12) United States Patent
Shahabdeen et al.

(10) Patent No.: US 7,684,954 B2
(45) Date of Patent: Mar. 23, 2010

(54) APPARATUS AND METHOD FOR CLASSIFICATION OF PHYSICAL ORIENTATION

(75) Inventors: Junaith Ahemed Shahabdeen, San Francisco, CA (US); Anita Gajjala, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 12/006,192

(22) Filed: Dec. 31, 2007

(65) Prior Publication Data

US 2009/0171615 A1 Jul. 2, 2009

(51) Int. Cl.
*G01P 15/00* (2006.01)
(52) U.S. Cl. .................................................. 702/141
(58) Field of Classification Search ............... 702/141, 702/183
See application file for complete search history.

(56) References Cited

OTHER PUBLICATIONS

Foerster, F, et al., "Motion pattern and posture: correctly assessed by calibrated accelerometers", *Behavior Research Methods, Instruments, & Computers*, 32(3), (Aug. 2000), 450-7.

Karantonis, D M, et al., "Implementation of a Real-Time Human Movement Classifier Using a Tri-axial Accelerometer for Ambulatory Monitoring", *IEEE Trans Inf Technol Biomed*, (Jan. 2006), 156-167.

Lin, Lao, et al., "Training Conditional Random Fields using Virtual Evidence Boosting", International joint conference on Artificial Intelligence, (2007).

Ludmilla, I K, et al., "Decision Templates for Multiple Classifier Fusion: An Experimental Comparison", *Pattern Recognition*, vol. 34, No. 2, 2001, ., Pattern Recognition, 34(2), (2001), 299-314.

Mantyjarvi, J, et al., "Recognizing human motion with multiple acceleration sensors", *IEEE International Conference on Systems, Man and Cybernetics*, (2001), 747-752.

Mathie, M J, et al., "Accelerometry: providing an integrated, practical method for long term, ambulatory monitoring of human movement", *Physiological Measurement*, vol. 25, No. 2, (Apr. 2004), R1-R20.

Mathie, M J, "Monitoring and Interpreting Human Movement Patterns Using a Triaxial accelerometer", *Ph.D. thesis.* Univ. New South Wales, Sydney, Australia, 2003.

Maurer, U, et al., "eWatch: A Wearable Sensor and Notification Platform", *IEEE International Workshop on Wearable and Implantable Body Sensor Networks*, (2006), 4 pgs.

(Continued)

*Primary Examiner*—Tung S Lau
*Assistant Examiner*—Xiuquin Sun
(74) *Attorney, Agent, or Firm*—Schwegman, Lundberg & Woessner, P.A.

(57) ABSTRACT

A state classifier uses learning obtained from a plurality of training algorithms each adapted to differentiate between states of physical orientation of an object in response to input data from an tri-axial accelerometer. At least two of the training algorithms are trained using data from an accelerometer mounted at a non-ideal angle. The classifier is trained to distinguish between the desired states from data collected from an tri-axial accelerometer device mounted at a plurality of respective angles with respect to a optimal axis on the object, wherein the angles are in the range of −180 degrees to +180 degrees. The classifier may include a plurality of classifiers and a decision fusion module used to combine the decisions from the respective classifiers to ascertain a state.

20 Claims, 10 Drawing Sheets

OTHER PUBLICATIONS

Mizell, David, "Using Gravity to Estimate Accelerometer Orientation", *IEEE International Symposium on Wearable Computers*, 2003, 2 pgs.

Polikar, R, "Ensemble Based Systems in Decision Making", *IEEE Circuits and Systems Magazine*, vol. 6, No. 3, (2006), 21-45.

Prill, T, et al., "Simultaneous assessment of posture and limb movements (e.g., periodic leg movements) with calibrated multiple accelerometry", *Physiological Measurement*, 27(10), (Oct. 2006), N47-N53.

Tapia, Emmanuel M., et al., "Activity Recognition in the Home Using Simple and Ubiquitous Sensors", In *Pervasive Computing*, vol. 3001/2004, (2004), 158-175.

| INPUT DATA | CLASSIFIER 1 | CLASSIFIER 2 | CLASSIFIER 3 | CLASSIFIER 4 | CLASSIFIER 5 | INFERENCE |
|---|---|---|---|---|---|---|
| +20DEGREESIT | MIX | MIX | +20DEGREELYING | -20DEGREESTAND 0DEGREESIT | -20DEGREESIT | SITTING |
| -20DEGREESIT | 0DEGREESIT | -20DEGREESIT | +20DEGREELYING 0DEGREELYING | +20DEGREESIT | -20DEGREESIT | SITTING |
| 0DEGREESIT | 0DEGREESIT, +20DEGREESIT | 0DEGREESIT | +20DEGREELYING | 0DEGREESIT | -20DEGREESIT | SITTING |
| +20DEGREESTAND | +20DEGREESTAND 0DEGREESTAND | 0DEGREESTAND 0DEGREESIT | +20DEGREELYING | -20DEGREESTAND 0DEGREESIT | -20DEGREESIT | STANDING |
| -20DEGREESTAND | 0DEGREESIT, +20DEGREESIT | -20DEGREESTAND 0DEGREESIT | +20DEGREELYING 0DEGREELYING -20DEGREELYING | -20DEGREESTAND 0DEGREESIT | -20DEGREESIT | STANDING |
| 0DEGREESTAND | 0DEGREESTAND | -20DEGREESTAND 0DEGREESIT | +20DEGREELYING | -20DEGREESTAND 0DEGREESIT | -20DEGREESIT 0DEGREESIT | STANDING |
| +20DEGREELYING | 0DEGREESIT | -20DEGREESIT | +20DEGREELYING | +20DEGREELYING | -20DEGREESIT | LYING |
| -20DEGREELYING | 0DEGREESIT | -20DEGREESIT | -20DEGREELYING | +20DEGREELYING | 0DEGREELYING | LYING |
| 0DEGREELYING | 0DEGREESIT | -20DEGREESIT | 0DEGREELYING | +20DEGREELYING | 0DEGREELYING | LYING |

| SITTING | 80.52% | STANDING |
| --- | --- | --- |
| STANDING | 99.23% | SITTING |
| LYING | 100% | |

APPARATUS AND METHOD FOR CLASSIFICATION OF PHYSICAL ORIENTATION

TECHNICAL FIELD

The disclosed subject matter relates generally to accelerometer devices, and more particularly to accelerometer devices used to determine the position or orientation of an object or person.

BACKGROUND

An accelerometer is a device for measuring the total specific external force on a sensor. This is sometimes referred to as the acceleration. A DC-coupled accelerometer sitting still on a table top has zero acceleration but will read the acceleration due to earth's gravity at that location, which is nominally one g. Accelerometers are thus useful in a wide variety of applications, including inertial navigation systems or for measuring acceleration due to gravity (inclination).

BRIEF DESCRIPTION OF THE DRAWINGS

FIG. 7 illustrates a confusion matrix table for the classification model of FIG. 6 according to the inventive subject matter disclosed herein.

FIG. 8 illustrates an accuracy and confusion table according to the inventive subject matter disclosed herein.

DETAILED DESCRIPTION

In the following detailed description, numerous specific details are set forth in order to provide a thorough understanding of the inventive subject matter. However it will be understood by those of ordinary skill in the art that the present invention may be practiced without these specific details. In other instances, well-known methods, procedures, components and circuits have not been described in detail so as not to obscure the present invention. Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the system's registers and/or memories into other data similarly represented as physical quantities within the system's memories, registers or other such information storage, transmission or display devices. In addition, the term "plurality" may be used throughout the specification to describe two or more components, devices, elements, parameters and the like.

Figure 1A:
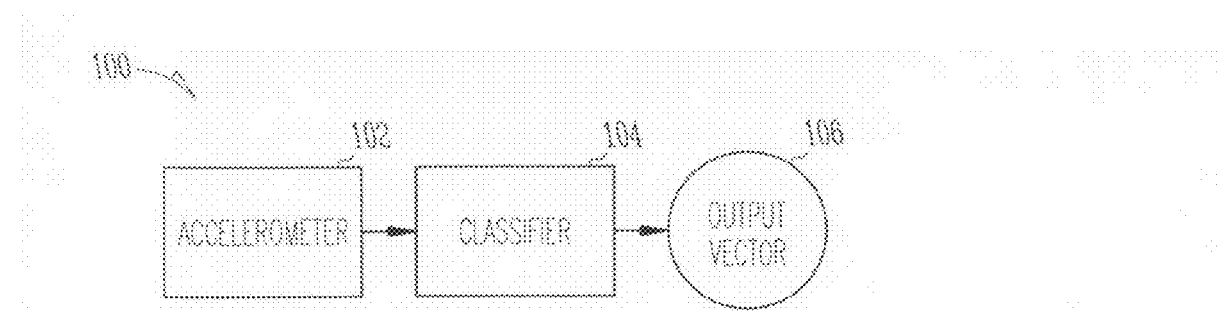
FIG. 1a illustrates a schematic block diagram of a sedentary state classifier device according to the inventive subject matter disclosed herein.
Figure 1B:
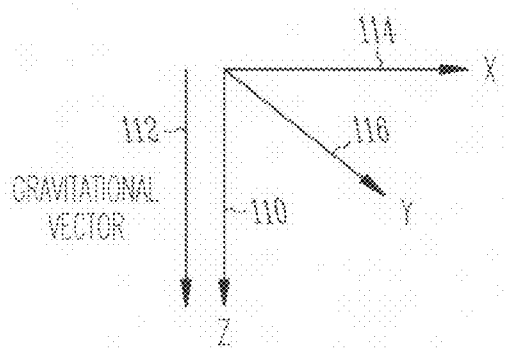
FIG. 1b illustrates the orientation of the axis of a tri-axial accelerometer according to the inventive subject matter disclosed herein.
Figure 1C:
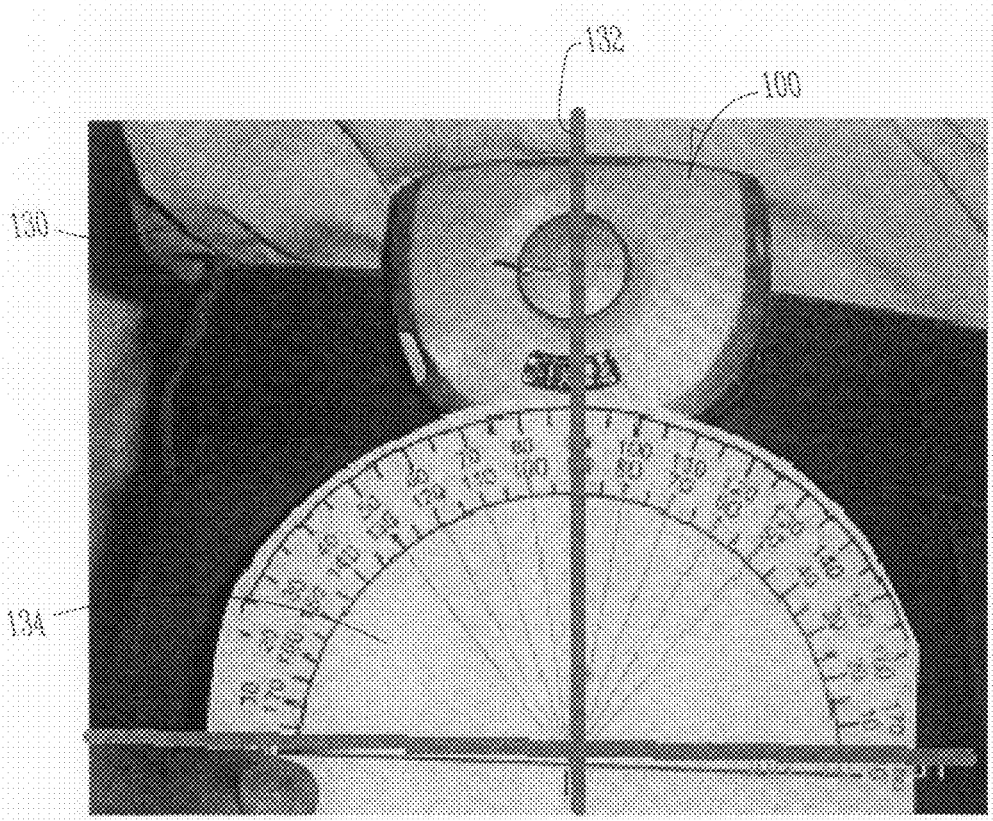
FIG. 1c illustrates a perspective view of a classifier device mounted on a human subject and corresponding accelerometer axis assumptions according to the inventive subject matter disclosed herein.

Referring now to FIG. 1a which illustrates a schematic diagram of a state classification device 100 used to classify different states of physical orientation of an object, for example but not limited to the sedentary states of a human subject, and in particular the states of sitting, standing or laying. Classification device 100 includes an accelerometer 102 that outputs measurements to a classifier 104 that in turn produces an output vector 106 that includes state classification data, in this particular example embodiment, sedentary state classification data. In one example embodiment, accelerometer 102 is a tri-axial accelerometer that can be used for the purpose of classification of states, where the z-axis 110 of accelerometer 102 is assumed to be aligned with the gravitational vector 112, as illustrated in FIGS. 1b and 1c. The x and y axes 114 and 116, respectively, are oriented at 90 degree angles with respect to the z axis. In FIG. 1c, device 100 is shown mounted on a human subject 130. In this embodiment, a 90 degree ray 132 shown on protractor 134 is aligned with the gravitational vector and the device 100 is also ideally aligned with the gravitational vector 112.

In use, classification device 100 is used to classify sedentary states, and is attached to a subject's body 130 and may, in one embodiment, continuously monitor the orientation thereof. In this example embodiment, device 100 may generate periodic measurements that may be correlated with, for example but not by way of limitation, periodic heart rate measurements. This correlation enables analysis of a subject's cardiac performance in each of the sedentary states identified by the classification device 100. While the inventive subject matter has been described herein with respect to classifying sedentary states, it will be appreciated that in other embodiments a classification according to the inventive subject matter may classify other states, for example but not limited to walking or running. Further, while device 100 is presented herein as applied to classifying sedentary state, the device and method according to the inventive subject matter is in no way so limited, and may be used to classify any state of physical orientation of any object.

As described above, sedentary classification device 100 may include a tri-axial accelerometer. By determining the accelerometer axis angle with respect to the gravitational vector and an assumed axis orientation of the device 100 on the subject, device 100 may distinguish between sedentary level states. This determination is sensitive to the static component of the accelerometer, which is defined by the orientation of the device relative to the gravitational vector. However, because the device assumes a predetermined orientation of the tri-axial accelerometer device on the subject's body, any change in orientation of the device relative to the subject's body affects the accuracy of the results. In particular, changes in the mount angle on the subject adversely affect the inferences made as to the sedentary state of the subject.

Figure 2A:
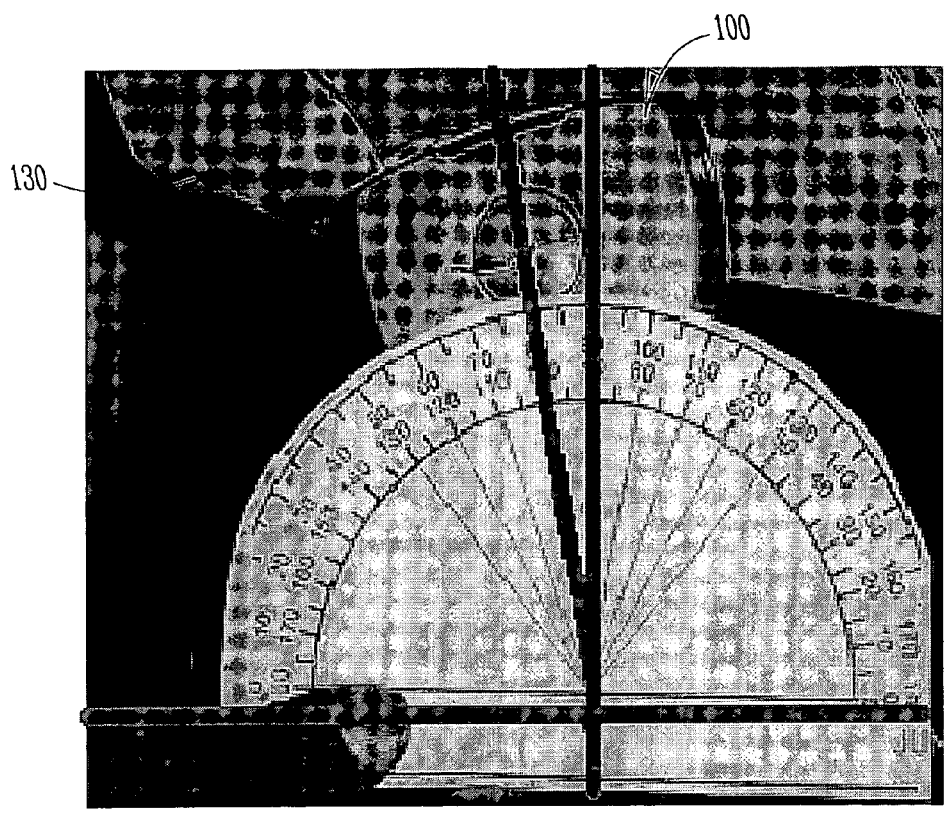
FIGS. 2a, 2b, 3a and 3b illustrate mount angles of various degrees of error for a classifier device according to the inventive subject matter disclosed herein.
Figure 2B:
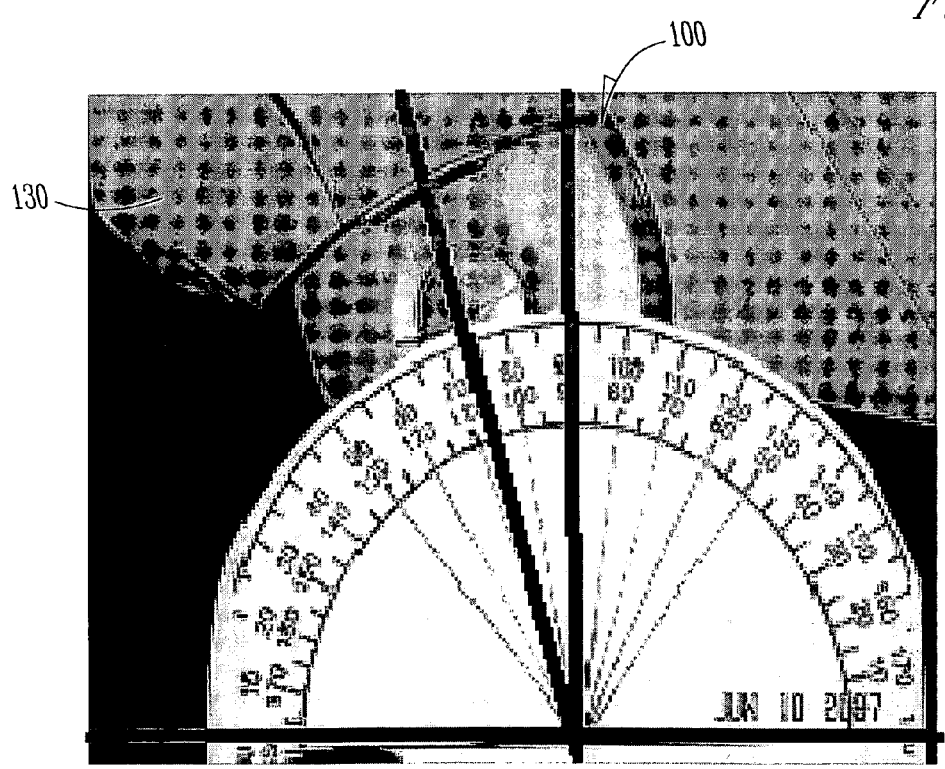
Figure 3A:
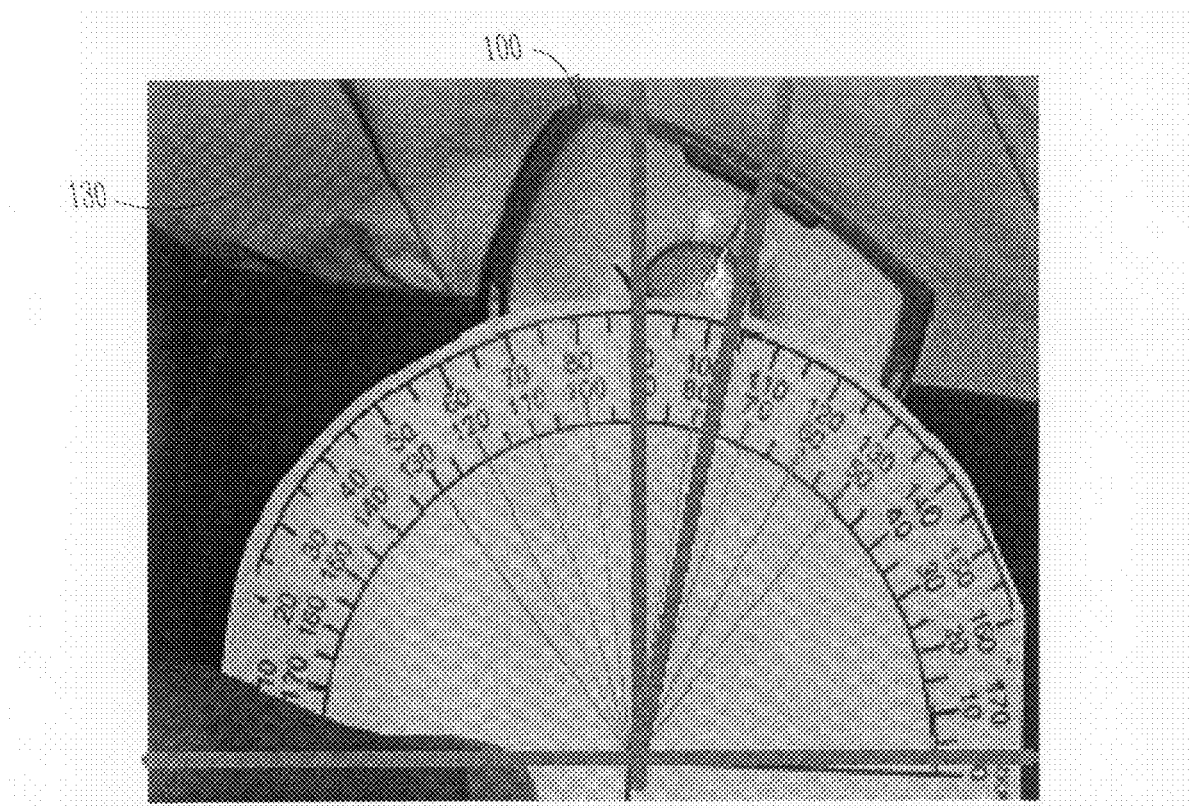
Figure 3B:
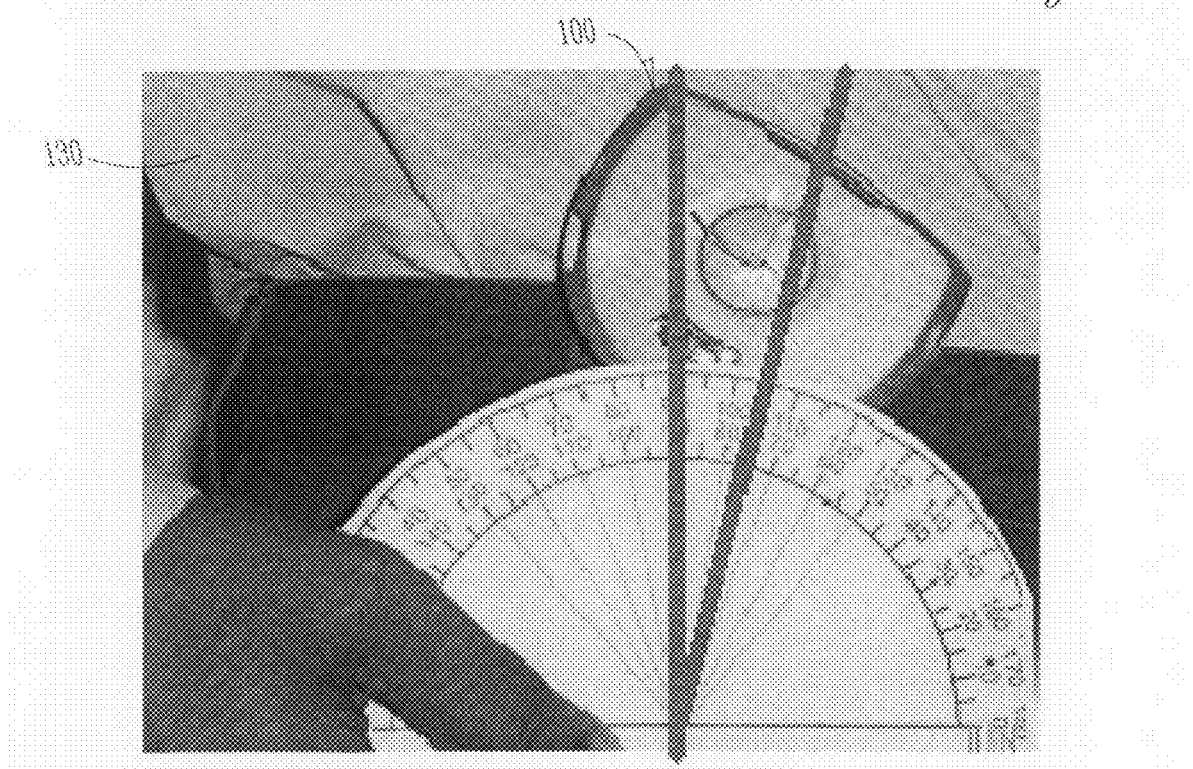
Figure 4A:
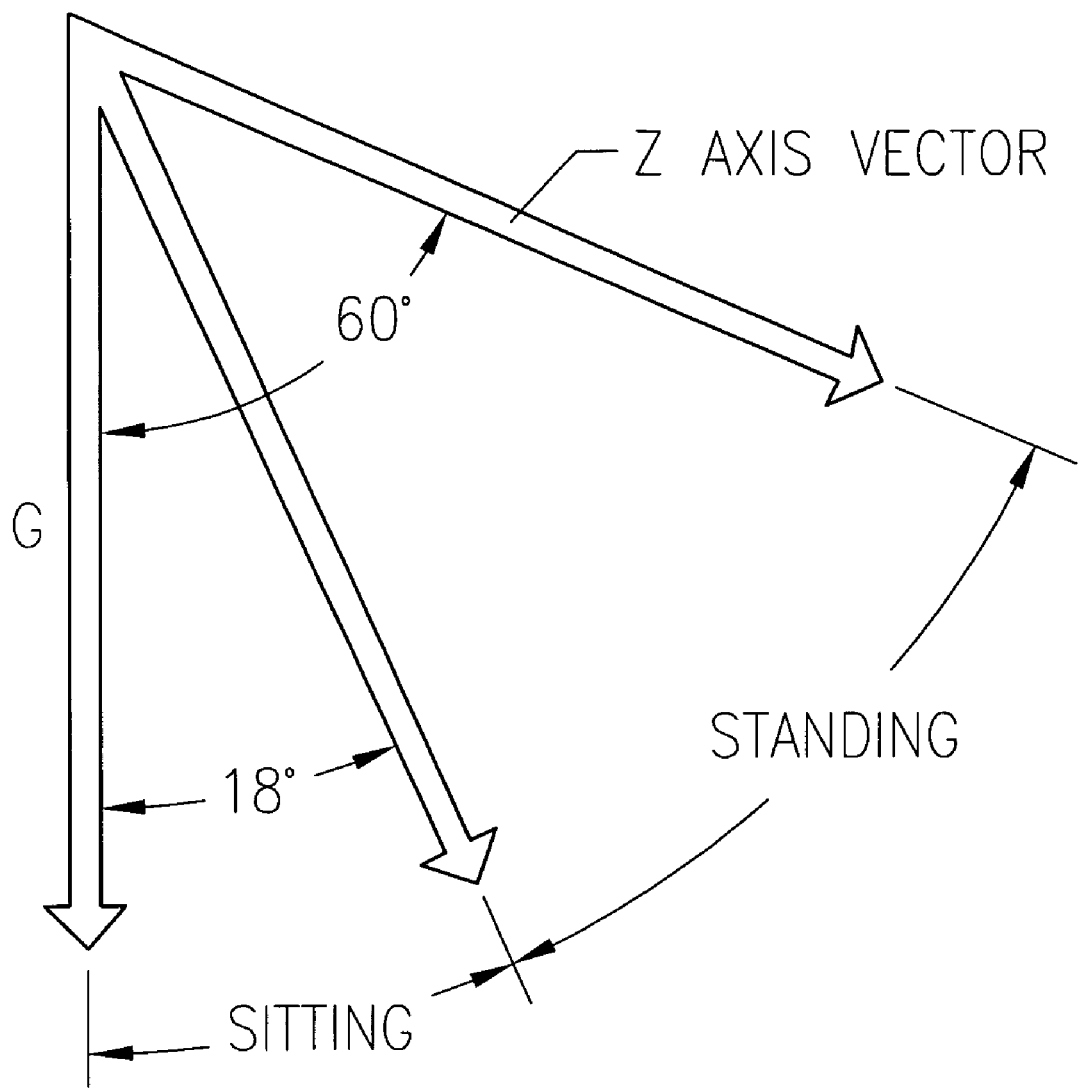
FIGS. 4a and 4b illustrate the tilt angles of the accelerometer and the gravitational vector for sitting and standing positions.
Figure 4B:
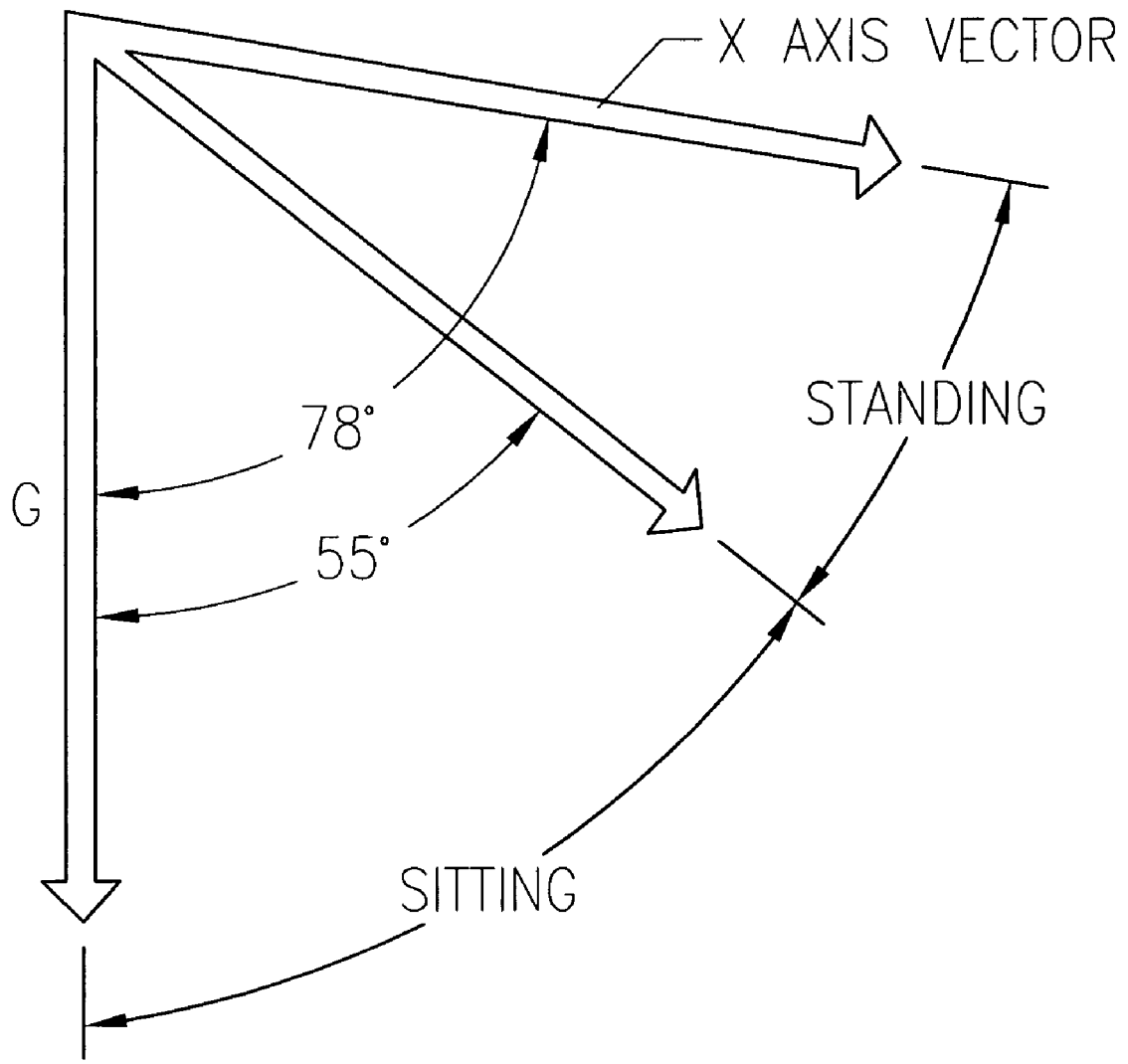

As may be appreciated from FIGS. 2a, 2b, 3a and 3b, maintaining the necessary or "ideal" mount angle of device 100 is sometimes difficult due to body movement or the way the device is mounted on the body. FIGS. 2a and 2b illustrate possible errors in mount angle of −10 degrees and −15 degrees due to tilting to the left of the device 100 and in turn the accelerometer 102. FIGS. 3a and 3b illustrate possible errors in mount angle of +10 degrees and +15 degrees due to tilting to the right. Any of these mounting angle anomalies can adversely affect the inference of a subject's sedentary position by classifier 108. FIG. 4a illustrates the tilt angles of the accelerometer 102 and the gravitational vector for sitting and standing positions. FIG. 4b illustrates the tilt angle between the x-axis and the gravitational vector for devices mounted as for example shown in FIGS. 2a, 2b, 3a and 3b. Using these measurements of tilt angle a classifier 108 can infer the sedentary state of a subject.

As explained herein below, the device 100 according to the inventive subject matter is adapted to accurately classify sedentary states even in the presence of deviances from the ideal mount angle. According to one example embodiment, classifier 108 may be trained for class boundaries using data collected from all possible orientations of both the mount angle and the sedentary states. The classifier 108 thus has additional knowledge to distinguish between the mount angles and is able to predict the right state, substantially or entirely independent of an ideal mount angle of the device on a subject.

According to one example embodiment, classifier 108 is trained offline to differentiate between various states defined in the training regimen based on features passed to it. Various training algorithms for a multi-class problem are discussed in the art and may be used for training purposes. Since learning the class boundaries is sensitive to the data passed to the training algorithm, it is essential to collect data for different mount angles of the device 100 on a subject. The output from the training algorithm may be in the form of a decision tree or a probability distribution, which may be used to build a classifier 108 that distinguishes the states.

Figure 5A:
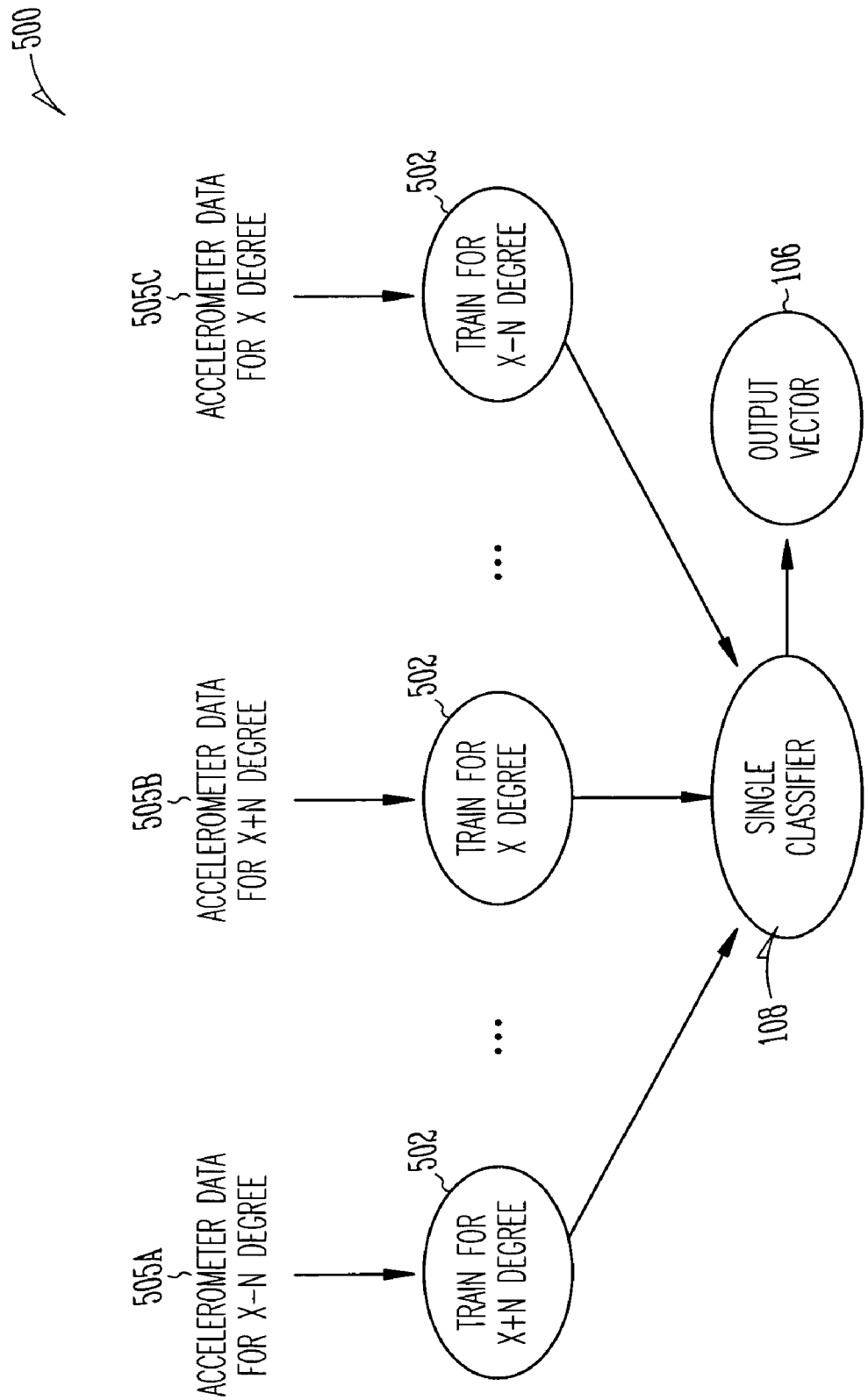
FIGS. 5a and 5b illustrate single and multiple classifier embodiments of a classifier device according to the inventive subject matter disclosed herein.

FIG. 5a demonstrates a training approach for a single classifier embodiment 500 of classifier 108 in the solution. In this embodiment, each training module 502 learns to distinguish between the desired states from the data 505a, 505b and 505c collected by mounting the device at an ideal angle and at less than ideal angles. This learning 506 from each training module 502 is fed into the single classifier of classifier 108 and it is used to differentiate between the desired states, i.e., sitting, standing and lying for the sedentary classifier according to the inventive subject matter. The data collection and training can be done in increments of X+/−10 degrees where X ideally starts with 0 degree with respect to gravity.

Figure 5B:
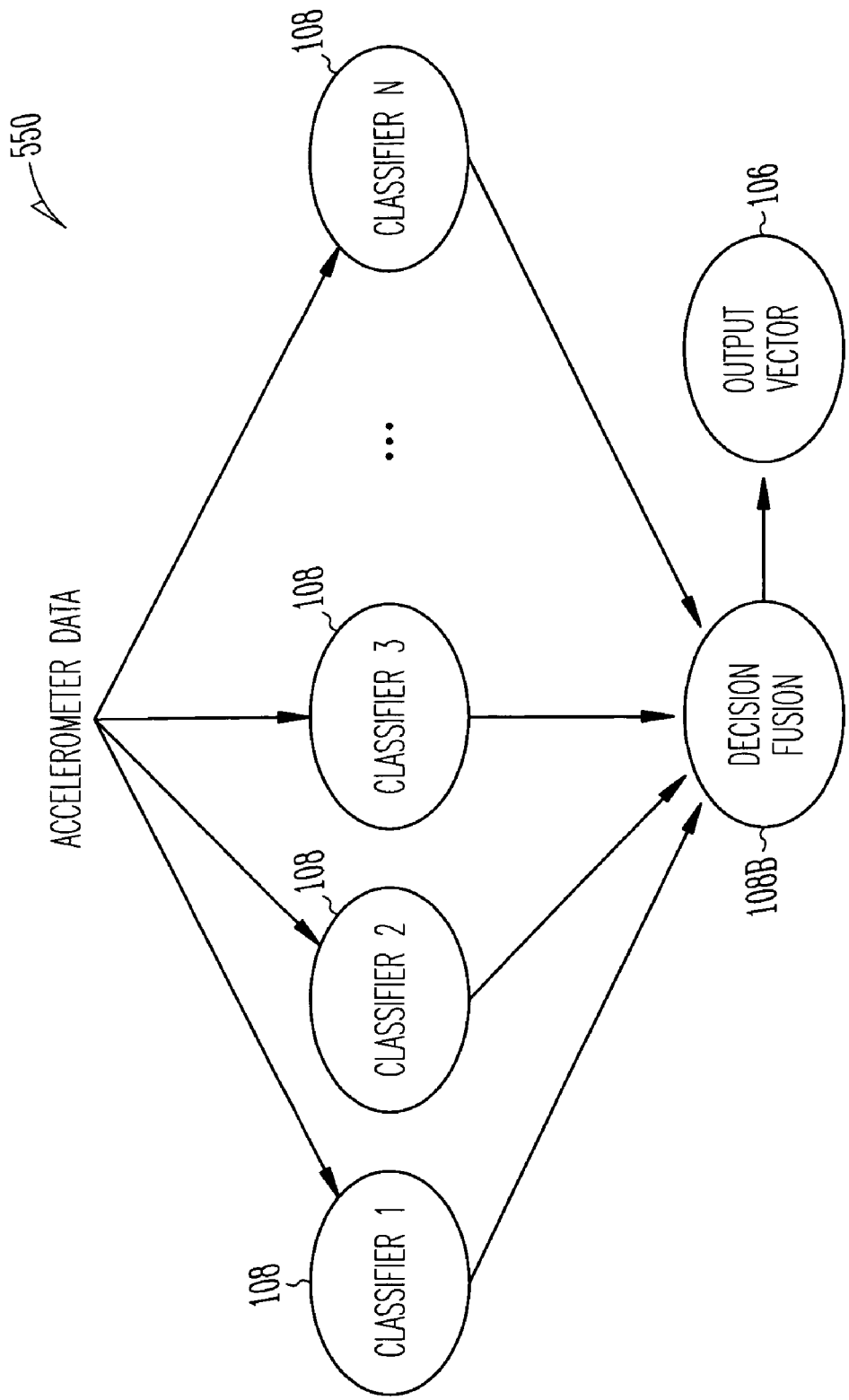

According to another example embodiment 550 illustrated in FIG. 5b, classifier 108 is implemented as a multiple classifier solution, wherein the output from each classifier 1–N can be combined to obtain the correct inference. In this case each classifier 1–N may be trained for the chosen mount angles as shown in FIG. 5a. For example, Classifier 1 may be trained for all positive mount angles (X+N degree) and it predicts the correct state given the accelerometer data for a positive mount angles. Similarly, Classifier 2 may be trained to predict the correct state for negative mount angles (X−N degree). A decision fusion module 108b combines the output from each of the classifiers 1–N for the final prediction. The confusion in decision for each classifier is considered to calculate the confidence level for each state. According to one example embodiment, the output vector 106 includes the confidence levels for all the states after combining the decision from the individual classifiers. The output can also be represented as the probability of each state given the input data.

Figure 6:
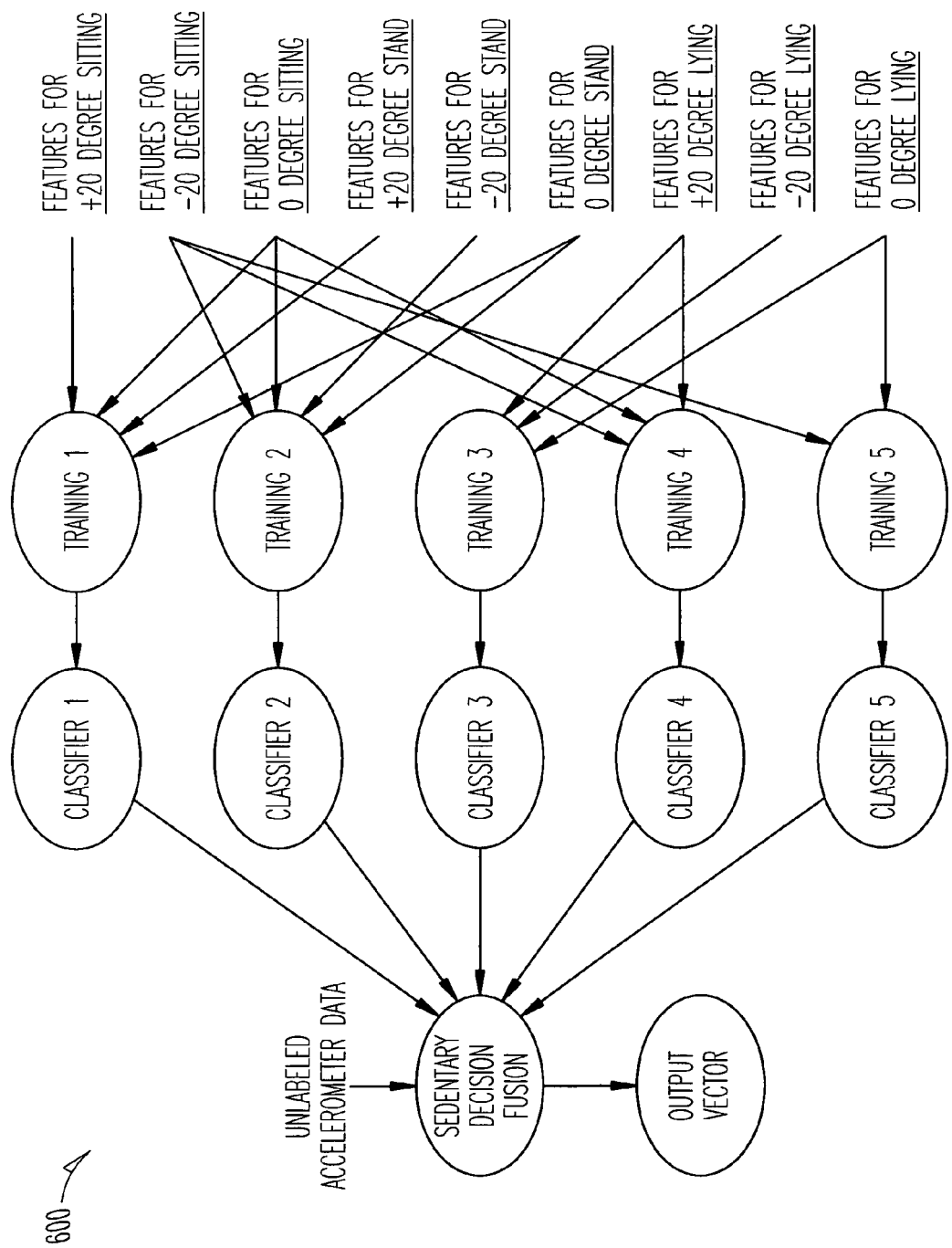
FIG. 6 illustrates a training and classification model for a multiple classifier system according to the inventive subject matter disclosed herein.

Referring to FIG. 6, there is illustrated a training and classification model 600 that combines the decision from the individual classifiers 1-5 and leverages the confusion matrix of the individual classifiers 1-5 for various inputs to infer the final probability distribution represented in the output vector. The confusion matrix for the combiner is described in Table 1 is illustrated in FIG. 7. According to one embodiment, for training purposes the mount angle can be incremented in steps of +/−10 degree. The intermediate states may be X+/−20 degree together with the original cases of X+/−0 degree. Thus the sedentary states are +20 degrees sitting, −20 degrees sitting, 0 degrees sitting, +20 degrees standing, −20 degrees sitting, standing, +20 degrees lying, −20 degrees lying, and lying. The reliability for each state for input data from four different subjects is described in Table 2 illustrated in FIG. 8.

Thus, according to the multiple classifier embodiments, each model may be trained based on appropriate features from different mount angles to build a classifier that can reliably distinguish between the states it is trained for. The models may be chosen so that they can reliably distinguish the given states, and the confusion can be used by the decision fusion to decide the final probability distribution.

Thus, there is described herein a sedentary classification device for classification of the sedentary states of a subject wearing the device. The classification device of the inventive subject matter provides for accurate classification of sedentary states like sitting, standing, and lying has valuable health applications among a wide range of other applications. The classification device may be used to generate data useful, for example, in analyzing cardiac performance, such as heart rate and blood pressure data, or human subjects. Alternatively, the device may be used, for example but not by way of limitation, in monitoring elderly and post-operative patients.

Furthermore, while the description herein is directed particularly to the task of sedentary classification, the inventive subject matter is in no way limited. In particular, the inventive subject matter is fully applicable to any classification problem that requires static acceleration or orientation. Accordingly, according to another example embodiment, the above described classification devices are applied to classification of any state of physical orientation using an accelerometer.

What is claimed is:

1. A method comprising:
   training a classifier device using learning obtained from a plurality of training algorithms each adapted to differentiate between states of physical orientation of an object in response to input data from a tri-axial accelerometer;
   wherein at least two of the training algorithms are trained using data from the tri-axial accelerometer when the tri-axial accelerometer is mounted on the object at non-ideal mount angles relative to an ideal mount angle having one axis of the tri-axial accelerometer aligned with a gravitational vector; and
   wherein the classifier device is trained to distinguish between the states of the object to which the tri-axial accelerometer device is mounted based on data collected from the tri-axial accelerometer device mounted at one or more of a plurality of respective angles with respect to the ideal mount angle on the object, wherein the plurality of respective angles are in the range of −180 degrees to +180 degrees.

2. A method according to claim 1 wherein the states are sedentary states and the object is a human subject, and the sedentary states are selected from the group: sitting, standing and lying.

3. A method according to claim 1 wherein the classifier includes a plurality of classifiers each adapted to differentiate between the states of the object under different mount angles of the tri-axial accelerometer.

4. A method according to claim 3 further including using decision fusion to predict a state of the object from classification information received from each of the classifiers.

5. A method according to claim 4 wherein the decision fusion combines the output from each of the classifiers for the prediction.

6. A method according to claim 5 wherein confusion in a decision for each classifier is considered to calculate a confidence level for at least one of the states.

7. A method according to claim 6 wherein the decision fusion produces an output vector including a confidence level for each of the states after combining the decision from the individual classifiers.

8. A method according to claim 1 wherein the non-ideal mount angle is in the range of −180 degrees to +180 degrees.

9. The method of claim 1, wherein the ideal mount angle and the non-ideal mount angles are independent from the states of physical orientation of the object.

10. An apparatus comprising:
a plurality of classifiers to distinguish between desired states of physical orientation of an object using data collected from an tri-axial accelerometer device mounted on the object, wherein each of the classifiers is configured receive data collected from the tri-axial accelerometer device when mounted on the object, wherein at least one classifier of the plurality of classifiers is trained using first training data and one or more second classifiers are trained using different training data, wherein the different training data correlates to one or more sets of data collected from the tri-axial accelerometer in one or more respective non-ideal mount angles on the object that differ from an ideal mount angle on the object having one axis of the tri-axial accelerometer aligned with a gravitational vector; and
a decision fusion module to identify one of the desired states from classification information received each of the classifiers based on state data collected from the tri-state accelerometer device;
wherein and the ideal mount angle and the at least one non-ideal mount are independent from the desired states of physical orientation of the object.

11. The apparatus according to claim 10 wherein the at least one non-ideal mount angle is in the range of −180 degrees to +180 degrees.

12. The apparatus according to claim 10 wherein the decision fusion module combines the output from each of the classifiers for the prediction.

13. The apparatus according to claim 12 wherein the decision fusion module considers confusion in a decision for each classifier to calculate a confidence level for at least one of the possible states.

14. The apparatus according to claim 13 wherein the decision fusion module produces an output vector including a confidence level for each of the possible states after combining the decisions from the individual classifiers.

15. The apparatus according to claim 10 wherein the desired states of physical orientation are states of physical orientation of a human subject.

16. The apparatus according to claim 15 wherein the desired states of physical orientation include sedentary states.

17. A method of determining a state of physical orientation of an object, the method comprising:
training a classifier to differentiate between a plurality of possible states of physical orientation of an object based on data collected from a tri-axial accelerometer when mounted on the object at different mount angles, wherein training the classifier comprises:
collecting first data from the tri-axial accelerometer mounted to the object at a first mount angle such that one axis of the tri-axial accelerometer is aligned to a gravitational vector;
collecting one or more second data from the tri-axial accelerometer mounted to the object at one or more second mount angles that differ from the first mount angle;
providing the first data to at least one training algorithm of a plurality of training algorithms to differentiate between possible states of physical orientation of the object;
providing the one or more second data to at least two training algorithms of the plurality of training algorithms to differentiate between the possible states;
generating an output from each of the plurality of training algorithms; and
providing each of the outputs to the classifier to train the classifier to differentiate between the plurality of possible states of the object;
wherein the first mount angle and the one or more second mount angles are independent from the plurality of possible states of physical orientation of the object.

18. The method of claim 17, wherein the output from each of the plurality of training algorithms comprises at least one of a decision tree and a probability distribution.

19. The method of claim 17, wherein the classifier comprises multiple classifiers, and wherein training the classifier comprises:
training each classifier to differentiate between the plurality of possible states of physical orientation of the object based on data collected from a tri-axial accelerometer at a selected mount angle from the first mount angle and the one or more second mount angles; and
combining outputs from each of the multiple classifiers in a decision fusion module to produce a predicted state from the plurality of possible states of physical orientation of the object.

20. The method of claim 19, wherein the predicted state comprises an output vector that includes confidence levels for each of the plurality of possible states.

* * * * *